United States Patent [19]

Ito et al.

[11] Patent Number: 5,213,806
[45] Date of Patent: May 25, 1993

[54] PHARMACEUTICAL COMPOSITION COMPRISING CALCIUM POLYCARBOPHIL

[75] Inventors: Yasuo Ito, Katsuyama; Hideo Kato, Fukui; Osamu Nagata, Fukui; Masaharu Yamazaki, Fukui; Takeo Ishibashi, Katsuyama; Masakazu Kitayama, Ohno, all of Japan

[73] Assignee: Hokuriku Pharmaceutical Co., Ltd., Fukui, Japan

[21] Appl. No.: 796,669

[22] Filed: Nov. 25, 1991

[30] Foreign Application Priority Data

Nov. 29, 1990 [JP] Japan .................................. 2-333368

[51] Int. Cl.$^5$ ........................ A61K 9/58; A61K 9/22; A61K 31/74
[52] U.S. Cl. ................................ 424/462; 424/78.01; 424/468; 514/867
[58] Field of Search ...................... 424/78.01, 441, 462, 424/468; 514/867

[56] References Cited

U.S. PATENT DOCUMENTS 3,297,664  1/1967  Miskel .............................. 424/441

FOREIGN PATENT DOCUMENTS 0192460  8/1986  European Pat. Off. .
0273209  7/1988  European Pat. Off. .
0428296  5/1991  European Pat. Off. .
0455561  11/1991  Fed. Rep. of Germany .
63-253027  10/1988  Japan .

OTHER PUBLICATIONS

Chemical Abstracts (109: 216036h) 1988.
*Handbook of Nonprescription Drugs*, 5th Edition, pp. 31–35, 1977.
Product publication for "FiberCon" Lederle Laboratories Division, American Cyanamid Company, 1986.
Hung Seng Ch'ng et al, "Bioadhesive Polymers as Platforms for Oral Controlled Drug Delivery II: . . . Synthesis" Journal of Pharmaceutical Science, vol. 74, No. 4, Apr. 1985 pp. 399–405.
Ivan E. Danhorf, "Pharmacology, Toxicology, Clinical Efficacy, and Adverse Effects of Calcium Polycarbophil, an Enteral Hydrosorptive Agent", Pharmacotherpy 1982, pp. 18–28 vol. 2 No. 1.

*Primary Examiner*—Frederick E. Waddell
*Assistant Examiner*—K. Weddington
*Attorney, Agent, or Firm*—Cushman, Darby & Cushman

[57] ABSTRACT

A pharmaceutical composition capable of being disintegrated in an acidic environment, which comprises calcium polycarbophil and 1 to 80% by weight of a cellulose derivative such as carboxymethylcellulose or low substituted hydroxypropylcellulose based on the calcium polycarbophil. The pharmaceutical composition in a form of a tablet, a capsule, or granules is useful as a bulk-forming laxative or an antidiarrheic agent since it can be disintegrated readily in the stomach and form a complete dispersion of polycarbophil in the digestive tract.

6 Claims, No Drawings

PHARMACEUTICAL COMPOSITION COMPRISING CALCIUM POLYCARBOPHIL

BACKGROUND OF THE INVENTION

1. Field of the Invention

The present invention relates to a pharmaceutical composition comprising calcium polycarbophil which is useful for the treatment of irritable bowel syndrome (IBS) as well as the treatment of constipation and diarrhea caused by dysfunction of the lower digestive tract.

More specifically, the present invention relates to a pharmaceutical composition capable of being disintegrated in an acidic environment, comprising the widely used bulk-forming laxative and an antidiarrheic agent calcium polycarbophil.

2. Description of the Related Art

Calcium polycarbophil is the calcium salt of polyacrylic acid cross-linked with divinyl glycol (Merck Index, 11th edition, No. 1704). The specification of the U.S. Pat. No. 3,297,664 describes the use of calcium polycarbophil for the treatment of constipation and diarrhea. Some physicochemical effects, described below, are considered to participate in the mechanism of action make calcium polycarbophil effective. When calcium polycarbophil is administered orally, carboxyl groups of polyacrylic acid moiety in calcium polycarbophil are converted to free acids, by the release of calcium ions, to form free polycarbophil in the acidic environment of gastric juice. Then, the free carboxyl groups formed are ionized after the free polycarbophil is transferred to the intestines and exposed to neutral or weekly basic enteral environment. As a result, the crosslinking polymer absorbs water to form colloidal bulk. During constipation, the water-containing colloidal bulk may ease defecation by softening and bulking the feces. On the other hand, during diarrhea, it brings about an antidiarrheal effect by lowering fluidity of the intestinal water (Pharmacotherapy 2(1), 18–28, 1982). Accordingly, the release of calcium ions from calcium polycarbophil in the stomach as well as the formation of uniform dispersion of the colloidal bulk in a digestive tract play important roles in making calcium polycarbophil effective.

However, free polycarbophil with free carboxyl groups has extremely high adhesive properties, so that free polycarbophil can be used as a mucoadhesive base material for the slow release of drugs (J. Pharm. Sci., 74, 399–405, 1985). Such properties may result in the problem that medicaments containing calcium polycarbophil cannot easily be disintegrated in an aqueous acidic solution such as, for example, artificial gastric juice (about pH 1.2). More specifically, calcium polycarbophil on the surface of a medicament is converted to polycarbophil by releasing calcium ions after contact is made with an acidic solution, and then a highly adhesive layer comprising free polycarbophil is formed on the surface of the medicament, which will block the penetration of water into the inside part of the medicament and will significantly restrain the medicament from disintegrating. As a result, when a medicament comprising calcium polycarbophil is administered orally, a uniform dispersion of its ingredients cannot be formed in the digestive tract because of the failure of disintegration, which may result in insufficient clinical effect by the medicament.

A chewable tablet (trade name: Mitrolan, A. H. Robins Co., U. S.) is one of commercially available compositions comprising calcium polycarbophil, which has been developed specifically to solve above-mentioned problems. The means adapted by chewable tablet are to prepare a disintegrated composition by mastication of the medicament and then transfer the masticated composition to the stomach so as to avoid an insufficient disintegration of the medicament in the stomach. However, the medicament is hardly be acceptable to patients because of its unpleasant taste during mastication and rough and unpleasant feelings on the palate.

Japanese Patent Unexamined Publication (hereinafter referred to as JP KOKAI) No. 1988 (Sho-63)/253027, assigned to American Cyanamide Company, discloses a pharmaceutical composition in the form of tablet, which comprises calcium polycarbophil together with microcrystalline cellulose (crystalline cellulose), magnesium stearate, crosslinked polyvinyl pyrrolidone (Crospovidone), polyvinyl pyrrolidone, silica gel (silicic anhydride), and stearic acid. The tablets further comprise caramel powder and are film-coated so that patients can take the tablets easily. An example of such commercially-available such tablets is Fibercon (trade name) from Lederle Laboratory. However, the effectiveness of these tablets is found to be insufficient, since the disintegration time of these tablets is not less than 60 minutes without exception when measured by the disintegration test adopted by the Japanese Pharmacopoeia.

SUMMARY OF THE INVENTION

An object of the present invention is to provide a pharmaceutical composition comprising calcium polycarbophil which can be disintegrated readily in an acidic environment.

Another object of the present invention is to provide a pharmaceutical composition useful as a bulk-forming laxative and an antidiarrheic, which comprises calcium polycarbophil and can be disintegrated readily in the stomach and form a complete dispersion of polycarbophil in the digestive tract.

A further object of the present invention is to provide a method for treating irritable bowel syndrome, constipation, or diarrhea comprising the step of administering the above pharmaceutical composition to a patient.

The inventors of the present invention have conducted various studies to achieve the foregoing objects and found that the objects can be effectively attained by providing a pharmaceutical composition comprising calcium polycarbophil and a cellulose derivative. The inventors have also found that the above pharmaceutical composition can be disintegrated readily in an acidic environment such as in the stomach when administered orally.

Thus, in accordance with the above objects, the present invention provides a pharmaceutical composition capable of being disintegrated in an acidic environment, which comprises calcium polycarbophil and 1 to 80% by weight of a cellulose derivative based on the calcium polycarbophil.

In accordance with another embodiment of the present invention, there is provided a pharmaceutical composition which is useful as a bulk-forming laxative and an antidiarrheic and is capable of being disintegrated readily in the stomach and forming a complete dispersion of polycarbophil in the digestive tract, which comprises calcium polycarbophil and 1 to 80% by weight of a cellulose derivative based on the calcium polycarbophil.

In accordance with yet another embodiment, the present invention provides a method for treating irritable bowel syndrome, constipation, or diarrhea which comprises the step of administering the above pharmaceutical composition to a patient.

Further objects, features and advantages of the present invention will become apparent from the Description of the Preferred Embodiments which follows, when read in light of the accompanying Examples.

DETAILED DESCRIPTION OF THE PREFERRED EMBODIMENTS

The calcium polycarbophil used in the present invention may have any degree of polymerization. An example of preferably used calcium polycarbophil is that described on pages from 218 to 219 of the United States Pharmacopoeia XXII.

The cellulose derivative used in the present invention is a macromolecular compound prepared by chemical derivatization of cellulose. Examples of the cellulose derivative include polycarboxymethylethers of cellulose such as, for example, carboxymethylcellulose, carboxymethylcellulose calcium, carboxymethylcellulose sodium, and croscarmellose sodium; hydroxypropylethers of cellulose such as, for example, hydroxypropylcellulose and low substituted hydroxypropylcellulose; methyl and hydroxypropyl mixed ethers such as, for example, hydroxypropylmethylcellulose; and methylethers of cellulose such as, for example, methylcellulose. These cellulose derivatives may be used alone or in combination. These cellulose derivatives are pharmaceutically acceptable ingredients described in the Japanese Pharmacopoeia or the Japanese Standards of Pharmaceutical Ingredients. The cellulose derivatives standardized by the Japanese Pharmacopoeia or the Japanese Standards of Pharmaceutical Ingredients are preferably used in the present invention.

The pharmaceutical composition of the present invention comprises calcium polycarbophil and from 1 to 80% by weight, preferably from 1 to 40% by weight of the cellulose derivative based on the weight of calcium polycarbophil. The pharmaceutical composition of the present invention, which can be prepared by formulating the ingredients in the above-described ratio, is capable of being disintegrated in an aqueous solution in a wide variety of pHs, particularly in an acidic environment such as in an acidic solution.

Where carboxymethylcellulose, low substituted hydroxypropylcellulose, carboxymethylcellulose calcium, or croscarmellose sodium are used as the cellulose derivative, the ratio of the cellulose derivative to calcium polycarbophil may preferably be from 2 to 40% by weight. Where hydroxypropylcellulose, hydroxypropylmethylcellulose, methylcellulose, or carboxymethylcellulose sodium are used as the cellulose derivative, the ratio of the cellulose derivative to calcium polycarbophil may preferably be from 1 to 10% by weight.

If the ratio of the cellulose derivative to calcium polycarbophil is lower than 1% by weight, the pharmaceutical composition will become unstable and the disintegration will be prolonged. If the ratio of the cellulose derivative to calcium polycarobophil is more than 80% by weight, the pharmaceutical composition will become too bulky to be taken easily by a patient.

The pharmaceutical composition of the present invention may further comprise a pharmaceutically acceptable carrier or coating other than the ingredients described above. Examples of the pharmaceutically acceptable carrier or coating include, for example, lactose, microcrystalline cellulose, D-mannitol, starch, sucrose, crospovidone, sodium carboxymethylstarch, stearic acid, magnesium stearate, talc, carnauba wax, white beeswax, polyvinylacetal diethylaminoacetate, and polyoxyl 40 stearate, which are useful as a excipient, a binder, a lubricant, and a polishing agent. These carrier or coating may be used in a ratio of not more than 300% by weight based on the calcium polycarbophil.

According to the present invention, there is also provided a method for preparing the pharmaceutical composition of the present invention, which comprises the steps of adding the cellulose derivative and a pharmaceutically acceptable optional carrier or coating to a prescribed amount of calcium polycarbophil, mixing the ingredients in a mixer, such as, for example, a twin-cylinder mixer to obtain a uniform dispersion for the preparation of the pharmaceutical composition of the present invention. The pharmaceutical composition of the present invention may be in a form of, for example, a tablet, a capsule, or granules.

Where two or more different cellulose derivatives are used for the preparation of the dispersion, each cellulose derivative may be independently added to calcium polycarbophil, or alternatively, the cellulose derivatives may be mixed to prepare a mixture of the cellulose derivatives before being added to calcium polycarbophil. The mixing process may generally be carried out at a temperature of not more than 40° C., preferably at room temperature, under a preferable relative humidity of not more than 75%.

The above-described dispersion may optionally be granulated. The granulation may be carried out by shattering, extruding, agitating, and/or tumbing the powdered dispersion obtained in the manner described above, together with a solvent such as, for example, water, ethanol, or isopropanol in a ratio of not more than 100% by weight based on calcium polycarbophil; drying the granules at a temperature of from 40° to 80° C., for 1 to 24 hours; or alternatively, granulating the dispersion and drying the granules in a fluidized bed granulating and drying apparatus at a temperature of from 40° to 80° C. for 15 to 120 minutes; and lastly followed by passing through a screen, if desired. Generally, granules having a particle size of from about 50 to 2,000 μm are preferable. The granules may further be mixed with the remaining amount of cellulose derivative and other additives which are commonly used as pharmaceutically acceptable carriers or coatings.

The pharmaceutical composition of the present invention can be prepared by compressing the powdered dispersion or granules described above by the method well known to a person skilled in the art to obtain a tablet, or alternatively, filling the powdered dispersion or granules in capsules such as, for example, gelatin hard capsules or gelatin soft capsules to obtain a pharmaceutical composition in the form of capsule. These pharmaceutical compositions such as, for example, tablets, capsules, or granules are readily disintegrated in the stomach when administered orally and are useful for the treatment of diseases of digestive tract which include for example, constipation and diarrhea.

The following is a non-limiting preferred example of the method for preparing the pharmaceutical composition of the present invention. Not more than 60% by weight of the cellulose derivative is added to calcium polycarbophil, and after 2 to 100% by weight of water or ethanol is added the mixture, the resulting mixture is granulated. The granules are dried at from 50° to 60° C., for 5 to 20 hours to obtain granules having a particle size of from 50 to 500 μm. If necessary, an additional amount of the cellulose derivative is added to the granules and mixed to obtain the composition containing calcium polycarbophil and 1 to 80% by weight of cellulose derivative based on the calcium polycarbophil. After 10 to 50% by weight of microcrystalline cellulose or lactose, and 0.5 to 5% by weight of magnesium stearate are added to the composition obtained above, the mixture is compressed to obtain tablets or is filled into capsules to obtain the pharmaceutical composition in the form of capsule.

Where tablets or granules are prepared according to the above-described method, the pharmaceutical composition may be film-coated according to a method well known to a person skilled in the art. Examples of the coating material include, for example, hydroxypropylmethylcellulose, polyethylene glycol 6,000 (macrogol 6,000), and titanium oxide, which may be used in a ratio of not more than 20% by weight of the total weight of the tablet.

The above-described processes for preparing the pharmaceutical composition are given by way of illustration only and are not to be construed as limiting. Further, it is to be understood that the processes can be modified by one of ordinary skilled in the art within the scope of the present invention.

The pharmaceutical composition of the present invention, prepared according to the methods described above, is capable of being disintegrated in an acidic environment, for example, in an acidic solution having a pH of from 1 to 4. The pharmaceutical composition of the present invention can preferably be disintegrated in 60 minutes, preferably in 20 minutes in an artificial gastric juice such as, for example, the first test solution for disintegration described in the 11th edition of the Japanese Pharmacopoeia. The pharmaceutical composition disintegrated in the stomach can form a uniform dispersion in digestive tract. By virtue of these effects, the present composition can make calcium polycarbophil effective and is quite useful for the treatment of irritable bowel syndrome as well as the treatment of diseases of digestive tract such as, for example, constipation and diarrhea caused by dysfunction of lower digestive tract. Further, the present composition is useful as a medicament since it does not cause rough and unpleasant sensations on the palate and is sufficiently stable if stored for a long period. The dose of the pharmaceutical composition of the present invention for an adult patient may generally be from about 1 to 8 grams per day, in 1 to 4 oral administrations, which may be increased or decreased depending on the age or condition of the patient to be treated.

The present invention will be further illustrated by the following Examples. The Examples are given by way of illustration only and are not to be construed as limiting.

| Example 1 | |
| --- | --- |
| Calcium polycarbophil | 625 mg |
| Carboxymethylcellulose | 50 mg |
| Microcrystalline cellulose | a sufficient quantity |
| Magnesium stearate | 6 mg |
| total | 970 mg |

A portion of carboxymethylcellulose (about half of the total carboxymethylcellulose) was added to calcium polycarbophil and mixed at room temperature. To the mixture obtained, 7% by weight of water based on calcium polycarbophil was added, and then the mixture was granulated and dried at 50° C. for 10 hours. The granules were passed through a 18 mesh screen and the remaining amount of carboxymethylcellulose and microcrystalline cellulose were added to the granules mixed. After magnesium stearate was added to the granules, the resulting mixture was compressed to obtain tablets containing 625 mg of calcium polycarbophil per tablet.

| Example 2 | |
| --- | --- |
| Calcium polycarbophil | 625 mg |
| Carboxymethylcellulose | 12.5 mg |
| Microcrystalline cellulose | a sufficient quantity |
| Magnesium stearate | 6 mg |
| Film coating | |
| Hydroxypropylmethylcellulose | 20 mg |
| Polyethylene glycol 6000 | 5 mg |
| Titanium oxide | 5 mg |
| Total | 1000 mg |

A portion of carboxymethylcellulose (about half of the total carboxymethylcellulose) was added to calcium polycarbophil and mixed at room temperature. To the mixture obtained, 5% by weight of water based on calcium polycarbophil was added, and then the mixture was granulated and dried at 60° C. for 10 hours. The granules were passed through a 18 mesh screen and the remaining amount of carboxymethylcellulose and microcrystalline cellulose were added to the granules. After magnesium stearate was added to the granules and mixed, the resulting mixture was compressed to obtain tablets containing 625 mg of calcium polycarbophil per tablet, which were film-coated by using hydroxypropylmethylcellulose, polyethylene glycol 6000, and titanium oxide to afford film-coated tablets.

EXAMPLES 3-7

In the same manner as described in Example 2, tablets of Examples 3 to 7 were obtained.

| Example 8 | |
| --- | --- |
| Calcium polycarbophil | 625 mg |
| Carboxymethylcellulose | 75 mg |
| Hydroxypropylcellulose | 10 mg |
| Micromicrocrystalline cellulose | a sufficient quantity |
| Magnesium stearate | 6 mg |
| Film coating | |
| Hydroxypropylmethylcellulose | 20 mg |
| Polyethylene glycol 6,000 | 5 mg |
| Titanium oxide | 5 mg |
| Total | 1000 mg |

A portion of carboxymethylcellulose (about half of the total carboxymethylcellulose) and hydroxypropylcellulose were added to calcium polycarbophil and mixed at room temperature. To the mixture obtained, 7% by weight of water based on calcium polycarbophil was added, and then the mixture was granulated and dried at 50° C. for 12 hours. The granules were passed through a 18 mesh screen and the remaining carboxymethylcellulose and microcrystalline cellulose were added to the granules. After magnesium stearate was added to the granules, the resulting mixture was compressed to obtain tablets containing 625 mg of calcium polycarbophil per tablet, which were film-coated by using hydroxypropylmethylcellulose, polyethylene glycol 6000, and titanium oxide to afford film-coated tablets.

EXAMPLES 9 TO 14

In the same manner as described in Example 8, tablets of Examples 9 to 14 were obtained.

| Example 15 | |
|---|---|
| Calcium polycarbophil | 312.5 mg |
| Lactose | a sufficient quantity |
| Low-substituted hydroxypropylcellulose | 50 mg |
| Magnesium stearate | 5 mg |
| Total | 500 mg |

Calcium polycarbophil, lactose, and low-substituted hydroxypropylcellulose were mixed at room temperature and 20% by weight of ethanol based on calcium polycarbophil was added to the mixture, which was then granulated and dried at 50° C. for 12 hours. After the granules were passed through a 18 mesh screen, magnesium stearate was added to the granules and then the mixture was filled in capsules so that 312.5 mg of calcium polycarbophil was contained in one capsule.

In the same manner as described in Example 15, capsules of Examples 16 and 17 were obtained.

| Example 16 | |
|---|---|
| Calcium polycarbophil | 312.5 mg |
| Lactose | a sufficient quantity |
| Low-substituted hydroxypropylcellulose | 6.25 mg |
| Magnesium stearate | 5 mg |
| Total | 500 mg |
| Example 17 | |
| Calcium polycarbophil | 312.5 mg |
| Lactose | a sufficient quantity |
| Low-substituted hydroxypropylcellulose | 125 mg |
| Magnesium stearate | 6 mg |
| Total | 600 mg |
| Example 18 | |
| Calcium polycarbophil | 625 mg |
| Lactose | a sufficient quantity |
| Corn starch | 100 mg |
| Hydroxypropylcellulose | 6.25 mg |
| Film coating | |
| Hydroxypropylmethylcellulose | 40 mg |
| Polyethylene glycol 6,000 | 5 mg |
| Titanium oxide | 5 mg |
| Total | 1000 mg |

Lactose and corn starch were added to calcium polycarbophil and mixed at room temperature. Hydroxypropylcellulose was dissolved in 30% by weight of ethanol based on calcium polycarbophil, and the solution was then added to the above mixture to obtain granules. After being dried at 50° C. for 5 hours, the granules were passed through a 16 mesh screen. Film coating on the granules was carried out by using hydroxypropylmethylcellulose, polyethylene glycol 6,000 and titanium oxide to obtain film-coated granules.

In the same manner as described in Example 18, granules of Examples 19 to 22 were obtained.

| Example 19 | |
|---|---|
| Calcium polycarbophil | 625 mg |
| Lactose | a sufficient quantity |
| Corn starch | 100 mg |
| Hydroxypropylcellulose | 18.75 mg |
| Film coating | |
| Hydroxypropylmethylcellulose | 40 mg |
| Polyethylene glycol 6,000 | 5 mg |
| Titanium oxide | 5 mg |
| Total | 1000 mg |
| Example 20 | |
| Calcium polycarbophil | 625 mg |
| Lactose | a sufficient quantity |
| Corn starch | 100 mg |
| Hydroxypropylcellulose | 31.25 mg |
| Film coating | |
| Hydroxypropylmethylcellulose | 40 mg |
| Polyethylene glycol 6,000 | 5 mg |
| Titanium oxide | 5 mg |
| Total | 1000 mg |
| Example 21 | |
| Calcium polycarbophil | 625 mg |
| Lactose | a sufficient quantity |
| Corn starch | 100 mg |
| Carboxymethylcellulose | 200 mg |
| Hydroxypropylcellulose | 50 mg |
| Film coating | |
| Hydroxypropylmethylcellulose | 40 mg |
| Polyethylene glycol 6,000 | 5 mg |
| Titanium oxide | 5 mg |
| Total | 1200 mg |
| Example 22 | |
| Calcium polycarbophil | 500 mg |
| Lactose | a sufficient quantity |
| Sucrose | 250 mg |
| Hydroxypropylmethylcellulose | 30 mg |
| Film coating | |
| Hydroxypropylmethylcellulose | 30 mg |
| talc | 16 mg |
| Carnauba wax | 3.6 mg |
| Polyoxyl 40 stearate | 0.4 mg |
| Total | 1000 mg |
| Comparative Example 1 | |
| As Comparative Example 1, a pharmaceutical composition not containing a cellulose derivative was prepared as follows: | |
| Calcium polycarbophil | 625 mg |
| Micromicrocrystalline cellulose | a sufficient quantity |
| Magnesium stearate | 6 mg |
| Film coating | |
| Hydroxypropylmethylcellulose | 20 mg |
| Polyethylene glycol 6,000 | 5 mg |
| Titanium oxide | 5 mg |
| Total | 1000 mg |

To calcium polycarbophil, 4% by weight of water based on calcium polycarbophil was added and mixed at room temperature. The mixture was granulated and dried at 50° C. for 10 hours. After the granules were passed through a 18 mesh screen, microcrystalline cellulose was added and mixed with the granules. After magnesium stearate was added and mixed, the resulting powder was compressed to obtain tablets containing 625 mg of calcium polycarbophil per one tablet, which were then film-coated to afford film-coated tablets.

| Comparative Example 2 | |
|---|---|
| According to the method described in the JP KOKAI No. 1988 (Sho-63)/253027, Comparative Example 2 was prepared as follows: | |
| Calcium polycarbophil | 625 mg |
| Micromicrocrystalline cellulose | 195 mg |
| Magnesium stearate | 5.5 mg |
| Crospovidone | 50 mg |
| Caramel | 13 mg |

-continued

| Comparative Example 2 | |
|---|---|
| Polyvinyl pyrrolidone | 25 mg |
| Anhydrous silicic acid | 5 mg |
| Stearic acid | 15 mg |
| Total | 933.5 mg |

Caramel and polyvinyl pyrrolidone were added to calcium polycrobophil and then a portion of crospovidone (about three fifths of the total crospovidone) was added and mixed. The mixture was granulated by using warm water at a temperature of about 50° to 65° C., which was then dried at 50° C. for 6 hours. After the granules were passed through a 18 mesh screen, the remaining amount of crospovidgne, microcrystalline cellulose, and anhydrous silicic acid were added to the granules. After magnesium stearate and stearic acid were added to the granules, the mixture was compressed to obtain tablets containing 625 mg of calcium polycarbophil per one tablet.

COMPARATIVE EXAMPLE 3

Film coating was carried out on the tablets obtained by the process described in Comparative Example 2, by using 20 mg of hydroxypropylmethylcellulose, 5 mg of polyethylene glycol 6,000, and 5 mg of titanium oxide per one tablet to obtain film-coated tablets.

The degree of disintegration and the stability of the above-described pharmaceutical compositions were measured. Tables 1 and 2 summarize the ingredients contained in the pharmaceutical compositions tested.

Experiment 1: Disintegration test

Disintegration test was carried out according to the method described in the Japanese Pharmacopoeia, i.e., disintegration test procedure (2) preparations coated with sucrose or other suitable coating agents; procedure (4) capsules; and procedure (5) granules, by using the first fluid (artificial gastric juice) described in the Japanese Pharmacopoeia. The results are summarized in Table 3.

The pharmaceutical compositions of the present invention in the form of plain tablets, film-coated tablets, capsules, and granules had excellent degree of disintegration. The tablet of Comparative Example 2, which is described in JP KOKAI No. 1988 (Sho-63)-253027, and its film-coated tablet (Comparative Example 3), as well as Fibercon (trade name) did not disintegrate in 60 minutes because of gel formation in the glass tubes of the test apparatus.

Experiment 2: Stability test

In order to determine stabilities of the pharmaceutical composition under storage, disintegration tests were carried out on the pharmaceutical compositions in the form of film-coated tablet, which had been stored for one month at 40° C. under 75% RH (relative humidity) before disintegration test was carried out. The results obtained are shown in Table 4.

The disintegration time of the pharmaceutical composition of the present invention, which contains 2 to 80% by weight of the cellulose derivative based on calcium polycarbophil, was not prolonged after the storage. On the other hand, the disintegration time of film-coated tablet of Comparative Example 1 was significantly prolonged after storage, which shows the reduced stability of Comparative Example 1.

One of ordinary skill in the art will recognize that improvements and modifications may be made while remaining within the scope of the present invention. The scope and spirit of the present invention is determined solely by the appended claims.

TABLE 1

| Example No. | Example 1 | Example 2 | Example 3 | Example 4 | Example 5 | Example 6 | Example 7 |
|---|---|---|---|---|---|---|---|
| Sort of tablets | plain tablet | film-coated tablet | film-coated tablet | film-coated tablet | film-coated tablet | film-coated tablet | film-coated tablet |
| Content of Cellulose derivatives (weight/weight %) | 8 | 2 | 4 | 8 | 16 | 40 | 80 |
| Calcium Polycarbophil | 625 mg | 625 mg | 625 mg | 625 mg | 625 mg | 625 mg | 625 mg |
| Cellulose derivatives | CMC 50 mg | CMC 12.5 mg | CMC 25 mg | CMC 50 mg | CMC 100 mg | CMC 250 mg | CMC 500 mg |
| Microcrystalline Cellulose | a sufficient quantity | a sufficient quantity | a sufficient quantity | a sufficient quantity | a sufficient quantity | a sufficient quantity | a sufficient quantity |
| Magnesium Stearate | 6 mg | 6 mg | 6 mg | 6 mg | 6 mg | 6 mg | 6 mg |
| Film | | | | | | | |
| Hydroxypropyl Methylcellulose | — | 20 mg | 20 mg | 20 mg | 20 mg | 20 mg | 20 mg |
| Polyethylene Glycol 6000 | — | 5 mg | 5 mg | 5 mg | 5 mg | 5 mg | 5 mg |
| Titanium Oxide | — | 5 mg | 5 mg | 5 mg | 5 mg | 5 mg | 5 mg |
| Total | 970 mg | 1000 mg | 1000 mg | 1000 mg | 1000 mg | 1200 mg | 1500 mg |

CMC: Carboxymethylcellulose

TABLE 2

| Example No. | Example 8 | Example 9 | Example 10 | Example 11 |
|---|---|---|---|---|
| Sort of tablets | film-coated tablet | film-coated tablet | film-coated tablet | film-coated tablet |
| Content of Cellulose derivatives (weight/weight %) | 14 | 18 | 18 | 18 |
| Calcium Polycarbophil | 625 mg | 500 mg | 500 mg | 500 mg |
| Cellulose derivatives | CMC 75 mg HPC 10 mg | CMC 75 mg HPC 16 mg | CMC-Ca 75 mg HPC 16 mg | L-HPC 75 mg HPC 16 mg |
| Microcrystalline Cellulose | a sufficient quantity | a sufficient quantity | a sufficient quantity | a sufficient quantity |
| Magnesium Stearate | 6 mg | 6 mg | 6 mg | 6 mg |

TABLE 2-continued

| Film | | | | |
|---|---|---|---|---|
| Hydroxypropyl Methylcellulose | 20 mg | 18 mg | 18 mg | 18 mg |
| Polyethylene Glycol 6000 | 5 mg | 3 mg | 3 mg | 3 mg |
| Titanium Oxide | 5 mg | 2 mg | 2 mg | 2 mg |
| Total | 1000 mg | 785 mg | 785 mg | 785 mg |

| Example No. | Example 12 | Example 13 | Example 14 | Compar. Example 1 |
|---|---|---|---|---|
| Sort of tablets | film-coated tablet | film-coated tablet | film-coated tablet | film-coated tablet |
| Content of Cellulose derivatives (weight/weight %) | 18 | 18 | 18 | 0 |
| Calcium Polycarbophil | 500 mg | 500 mg | 500 mg | 625 mg |
| Cellulose derivatives | CCM-Na 75 mg HPC 16 mg | CMC 75 mg MC 16 mg | CMC 75 mg CMC-Na 16 mg | — |
| Microcrystalline Cellulose | a sufficient quantity | a sufficient quantity | a sufficient quantity | a sufficient quantity |
| Magnesium Stearate | 6 mg | 6 mg | 6 mg | 6 mg |
| Film | | | | |
| Hydroxypropyl Methylcellulose | 18 mg | 18 mg | 18 mg | 20 mg |
| Polyethylene Glycol 6000 | 3 mg | 3 mg | 3 mg | 5 mg |
| Titanium Oxide | 2 mg | 2 mg | 2 mg | 5 mg |
| Total | 785 mg | 785 mg | 785 mg | 1000 mg |

CMC: Carboxymethylcellulose, HPMC: Hydroxypropyl Methylcellulose,
HPC: Hydroxypropyl Cellulose, CMC-Ca: Carboxymethylcellulose Calcium,
L-HPC: Low Substituted Hydroxypropyl Cellulose, CCM-Na: Croscarmellose Sodium,
MC: Methylcellulose, CMC-Na: Carboxymethylcellulose Sodium

TABLE 3

Disintegration Test

| Content of Cellulose derivatives (weight/weight %) | Example No. | Sort of Preparations | Disintegration time (min) |
|---|---|---|---|
| 8 | Example 1 | plain tablet | 0.1~0.2 |
| 2 | Example 2 | film-coated | 6.7~15 |
| 4 | Example 3 | " | 4.3~6.8 |
| 8 | Example 4 | " | 1.3~2.9 |
| 16 | Example 5 | " | 0.6~1.2 |
| 40 | Example 6 | " | 1.0~2.1 |
| 80 | Example 7 | " | 2.2~3.1 |
| 14 | Example 8 | " | 2.5~3.1 |
| 18 | Example 9 | " | 2.1~2.4 |
| 16 | Example 15 | hard gelatin capsule | 2.3~3.9 |
| 2 | Example 16 | " | 6.3~13.5 |
| 40 | Example 17 | " | 2.5~4.6 |
| 1 | Example 18 | film-coated granule | 7.4~15 |
| 3 | Example 19 | " | 2.1~9.5 |
| 5 | Example 20 | " | 4.7~12 |
| 40 | Example 21 | " | 3.0~7.6 |
| 6 | Example 22 | " | 0.9~2.2 |
| — | Compar. Example 2 | tablet before coating (JP KOKAI 1988/253027) | ≧60 |
| — | Compar. Example 3 | film-coated tablet of Compar. Example 2 | ≧60 |
| — | Fibercon ® | | ≧60 |

TABLE 4

Stability Test

| Content of Cellulose derivatives (weight/weight %) | Example No. | Sort of Pharmaceutics | Disintegrating time (min) | |
|---|---|---|---|---|
| | | | at the time of the start | after stored for 1 month at 40° C. under 75% RH |
| 0 | Compar. Example 1 | film-coated tablet | 13~27 | ≧60 |
| 2 | Example 2 | " | 6.7~15 | 17~35 |
| 4 | Example 3 | " | 4.3~6.8 | 9.1~19 |
| 8 | Example 4 | " | 1.3~2.9 | 0.9~2.3 |
| 16 | Example 5 | " | 0.6~1.2 | 0.7~1.1 |
| 40 | Example 6 | " | 1.0~2.1 | 0.8~2.7 |

TABLE 4-continued

| | | Stability Test | | |
| | | | Disintegrating time (min) | |
| Content of Cellulose derivatives (weight/weight %) | Example No. | Sort of Pharmaceutics | at the time of the start | after stored for 1 month at 40° C. under 75% RH |
| --- | --- | --- | --- | --- |
| 80 | Example 7 | " | 2.2~3.1 | 2.0~2.9 |

What is claimed is:

1. A pharmaceutical composition capable of being disintegrated in an acidic environment, which comprises calcium polycarbophil mixed with 1 to 80% by weight of a cellulose derivative based on the calcium polycarbophil wherein the cellulose derivative is selected from the group consisting of polycarboxymethylethers of cellulose, hydroxypropylethers of cellulose, methyl and hydroxypropyl mixed ethers of cellulose, and methylethers of cellulose.

2. A pharmaceutical composition capable of being disintegrated in an acidic environment, which comprises calcium polycarbophil mixed with 1 to 80% by weight of a cellulose derivative based on the calcium polycarbophil.

3. The pharmaceutical composition according to claim 2, wherein the cellulose derivative is selected from the group consisting of carboxymethylcellulose, low-substituted hydroxypropylcellulose, carboxymethylcellulose calcium, carboxymethylcellulose sodium, croscarmellose sodium, hydroxypropylcellulose, hydroxypropylmethylcellulose, methycellulose, and mixtures thereof.

4. The pharmaceutical composition according to claim 2, wherein the composition is in the form of a tablet.

5. The pharmaceutical composition according to claim 2, wherein the composition is in the form of a capsule.

6. The pharmaceutical composition according to claim 2, wherein the composition is in the form of granules.

* * * * *